(12) United States Patent
Hwang et al.

(10) Patent No.: US 11,911,114 B2
(45) Date of Patent: Feb. 27, 2024

(54) ULTRASONIC PROBE AND ULTRASONIC IMAGING APPARATUS INCLUDING THE SAME

(71) Applicant: SAMSUNG MEDISON CO., LTD., Gangwon-do (KR)

(72) Inventors: Won-Soon Hwang, Hanam-si (KR); Min Seon Seo, Seongnam-si (KR); Won Seok Jang, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 124 days.

(21) Appl. No.: 17/441,536

(22) PCT Filed: Nov. 20, 2019

(86) PCT No.: PCT/KR2019/015978
§ 371 (c)(1),
(2) Date: Sep. 21, 2021

(87) PCT Pub. No.: WO2020/209461
PCT Pub. Date: Oct. 15, 2020

(65) Prior Publication Data
US 2022/0183763 A1 Jun. 16, 2022

(30) Foreign Application Priority Data
Apr. 11, 2019 (KR) .................. 10-2019-0042452

(51) Int. Cl.
*A61B 34/00* (2016.01)
*A61B 34/20* (2016.01)
(Continued)

(52) U.S. Cl.
CPC ............ *A61B 34/20* (2016.02); *A61B 8/0841* (2013.01); *A61B 8/4483* (2013.01); *B06B 1/0644* (2013.01); *A61B 2034/2051* (2016.02)

(58) Field of Classification Search
CPC ..... A61B 34/20; A61B 8/0841; A61B 8/4483; A61B 2034/2051; B06B 1/0644
See application file for complete search history.

(56) References Cited

U.S. PATENT DOCUMENTS 9,459,087 B2 10/2016 Dunbar et al.
10,026,338 B2 7/2018 Savitsky et al.
(Continued)

FOREIGN PATENT DOCUMENTS

JP 2002-136514 A 5/2002
JP 2002136514 A * 5/2002
(Continued)

OTHER PUBLICATIONS

Extended European Search Report dated Apr. 12, 2022 issued in European Patent Application No. 19924583.8.
(Continued)

*Primary Examiner* — Shahdeep Mohammed
*Assistant Examiner* — Adam D. Kolkin
(74) *Attorney, Agent, or Firm* — Morgan, Lewis & Bockius LLP (57) ABSTRACT

An ultrasonic probe that acquires an ultrasonic image to diagnose or treat an object, and an ultrasonic imaging apparatus including the same, wherein the ultrasonic probe includes a case, a transducer disposed inside the case to generate ultrasonic waves, a biopsy needle inserted into an object in the vicinity of the case, and a sensor unit including a sensor provided to measure a position of the biopsy needle and disposed inside the transducer, wherein the transducer includes a piezoelectric layer configured to generate ultrasonic waves, a sound absorbing layer disposed on one side of the piezoelectric layer to absorb the ultrasonic waves generated from the piezoelectric layer, and a sound absorbing member disposed on one side of the sound absorbing
(Continued)

layer, and the sensor unit is disposed inside the sound absorbing member.

14 Claims, 10 Drawing Sheets

(51) Int. Cl.
    *A61B 8/08*         (2006.01)
    *A61B 8/00*         (2006.01)
    *B06B 1/06*         (2006.01)

(56) References Cited

U.S. PATENT DOCUMENTS

| | | | |
|---|---|---|---|
| 2004/0236223 A1* | 11/2004 | Barnes | A61B 8/4254 600/459 |
| 2006/0004290 A1 | 1/2006 | Smith et al. | |
| 2006/0241467 A1* | 10/2006 | Takeda | G10K 9/18 600/459 |
| 2009/0248041 A1* | 10/2009 | Williams | A61B 8/12 606/130 |
| 2011/0282188 A1* | 11/2011 | Burnside | A61B 34/25 600/424 |
| 2013/0285174 A1* | 10/2013 | Sako | A61B 8/4444 257/416 |
| 2013/0338503 A1 | 12/2013 | Cohen et al. | |
| 2014/0128739 A1 | 5/2014 | Sundaran et al. | |
| 2016/0007961 A1 | 1/2016 | Lee et al. | |

FOREIGN PATENT DOCUMENTS

| | | |
|---|---|---|
| JP | 2013-169382 A | 9/2013 |
| JP | 2018-023677 A | 2/2018 |
| KR | 10-2012-0093603 A | 8/2012 |
| KR | 10-2016-0084255 A | 7/2016 |
| KR | 20160084255 A * | 7/2016 |
| KR | 10-2019-0035263 A | 4/2019 |
| WO | 2019/040045 A1 | 2/2019 |

OTHER PUBLICATIONS

International Search Report dated Mar. 20, 2020 issued in International Patent Application No. PCT/KR2019/015978 (with English translation).

Office Action dated Oct. 16, 2023 for counterpart European Patent Application No. 19924583.8.

* cited by examiner

ULTRASONIC PROBE AND ULTRASONIC IMAGING APPARATUS INCLUDING THE SAME

CROSS-REFERENCE OF RELATED APPLICATIONS

This application is the U.S. National Phase under 35 U.S.C. § 371 of International Patent Application No. PCT/KR2019/015978, filed on Nov. 20, 2019, which in turn claims the benefit of Korean Application No. 10-2019-0042452, filed on Apr. 11, 2019, the entire disclosures of which applications are incorporated by reference herein.

TECHNICAL FIELD

The present disclosure relates to an ultrasonic probe that acquires an ultrasonic image to diagnose or treat an object, and an ultrasonic imaging apparatus including the same.

BACKGROUND ART

An ultrasonic imaging apparatus may include an apparatus that irradiates an ultrasonic signal from a body surface of an object toward a target site in the body and obtains an image of a cross-section of soft tissues or blood flow in a non-invasive manner by using information of a reflected ultrasonic signal (ultrasonic echo signal).

In general, the ultrasonic imaging apparatus may include a main body, and an ultrasonic probe for transmitting an ultrasonic signal to an object to be diagnosed and receiving a signal reflected from the object.

During diagnosis by an ultrasonic imaging apparatus, a needle biopsy may be performed on a region suspected of having a tumor or the like inside an object. The needle biopsy may be performed using a needle inserted into the inside of the object to collect tissue.

However, when the needle inserted into the object deviates from the ultrasonic image by the ultrasonic probe, a normal tissue or organ of the object may be damaged.

That is, because the needle moving forward of the ultrasonic probe may not be well distinguished from the surrounding tissue in the ultrasonic image, and it may be difficult for a user to grasp a movement distance of the needle when a route through which the needle is inserted is not properly displayed on a display projected by the ultrasonic imaging apparatus, the possibility of medical accidents may increase.

Therefore, it may be necessary for the needle biopsy to precisely guide the needle to the desired position of the object, and it may be beneficial for the needle biopsy to track or monitor the needle to ensure holding the needle in the desired position.

The ultrasonic probe may include a sensor unit provided to measure a position and movement distance of the needle. The sensor unit may measure a position and movement distance of the needle using mechanical, electrical, magnetic characteristics, and the like.

In general, in order to mount the sensor unit provided to detect a magnetic field of a magnetized needle to the ultrasonic probe, the sensor unit may be located on an outer surface of a transducer, or a separate mounting case provided to mount the sensor unit may be required.

DISCLOSURE

Technical Problem

The present disclosure is directed to providing an improved ultrasonic probe to improve the stability of biopsy by accurately measuring a position and movement distance of a needle, and an ultrasonic imaging apparatus including the same.

The present disclosure is directed to providing an improved ultrasonic probe in which a sensor unit for detecting a magnetic field of a magnetized needle is disposed inside a transducer, and an ultrasonic imaging apparatus including the same.

The present disclosure is directed to providing an improved ultrasonic probe to integrate a ground substrate, a signal substrate, or a sensor substrate as one substrate, and an ultrasonic imaging apparatus including the same.

Technical Solution

An aspect of the present disclosure provides an ultrasonic probe including a case, a transducer disposed inside the case and generating ultrasonic waves, a biopsy needle inserted into an object at a position adjacent to the case, and a sensor unit including a sensor provided to measure the position of the biopsy needle and disposed inside the transducer, wherein the transducer includes a piezoelectric layer configured to generate ultrasonic waves, a sound absorbing layer disposed on one side of the piezoelectric layer to absorb the ultrasonic waves generated from the piezoelectric layer, and a sound absorbing member disposed on one side of the sound absorbing layer, and the sensor unit is disposed an inside of the sound absorbing member.

The biopsy needle may be magnetized, and the sensor may be configured to measure the position of the magnetized biopsy needle through a magnetic field generated by the magnetized biopsy needle.

The transducer may further include a ground substrate disposed on one side of the piezoelectric layer, and a signal substrate disposed on the other side of the piezoelectric layer to be disposed at an inner side of the ground substrate, and the sensor unit may further include a sensor substrate disposed at an inner side of the signal substrate to mount the sensor.

The transducer may further include a signal substrate disposed adjacent to the piezoelectric layer, and the sensor may be mounted on an inner surface of the signal substrate.

The transducer may further include a ground substrate disposed adjacent to the piezoelectric layer, and the sensor may be mounted on an inner surface of the ground substrate.

The sensor substrate may include a first sensor substrate provided on one side of the inside of the sound absorbing member, and a second sensor substrate provided on the other side of the inside of the sound absorbing member to be spaced apart from the first sensor substrate.

The sensor may include a first sensor mounted on the first sensor substrate and a second sensor mounted on the second sensor substrate, and the first sensor and the second sensor may face each other.

The sensor may include a first sensor mounted on the first sensor substrate and a second sensor mounted on the second sensor substrate, and the first sensor and the second sensor may be disposed adjacent to an inner surface of the sound absorbing member to face the signal substrate.

The sensor unit may further include a heat radiation sheet disposed on an inner surface of the sensor substrate.

The sensor unit may further include a stabilizer connected to the heat radiation sheet so that the heat radiation sheet radiates heat from the sensor and disposed at one end of the sound absorbing member.

The sensor unit may be disposed inside a cover member provided to cover the outside of the transducer to prevent a disinfectant from penetrating into the sensor unit.

A distance by which the first sensor substrate and the second sensor substrate are spaced apart from each other may be 10 to 60 times an acoustic wavelength of the transducer.

The ultrasonic probe may further include a lens provided to transmit an ultrasonic signal generated from the transducer to the outside of the case, wherein the lens and the case may be combined by a molding process.

The transducer may further include an acoustic layer having a non-magnetic material to prevent interference with the reception of the magnetic field of the sensor unit.

Another aspect of the present disclosure provides an ultrasonic probe including a case, a transducer including a piezoelectric layer disposed inside the case and configured to generate ultrasonic waves, a sound absorbing layer disposed on one side of the piezoelectric layer to absorb the ultrasonic waves generated from the piezoelectric layer, and a sound absorbing member disposed on one side of the sound absorbing layer, a magnetized biopsy needle inserted into an object in the vicinity of the case, and a sensor unit disposed inside the sound absorbing member to measure a position of the magnetized biopsy needle.

The transducer may further include a ground substrate disposed on one side of the piezoelectric layer, and a signal substrate disposed on the other side of the piezoelectric layer to be disposed at an inner side of the ground substrate, and the sensor unit may include a sensor provided to measure the position of the magnetized biopsy needle, and a sensor substrate disposed at an inner side of the signal substrate to mount the sensor.

The sensor substrate may include a first sensor substrate provided on one side of the inside of the sound absorbing member, and a second sensor substrate provided on the other side of the inside of the sound absorbing member to be spaced apart from the first sensor substrate.

Another aspect of the present disclosure provides an ultrasonic imaging apparatus including a main body, an ultrasonic probe connected to the main body to transmit and receive ultrasonic signals from and to an object, and a position detection unit provided to detect a position of the ultrasonic probe, wherein the ultrasonic probe includes a transducer including a piezoelectric layer configured to generate ultrasonic waves, a sound absorbing layer disposed on one side of the piezoelectric layer to absorb the ultrasonic waves generated from the piezoelectric layer, and a sound absorbing member disposed on one side of the sound absorbing layer, and the position detection unit includes a first position detection unit disposed inside the sound absorbing member, and a second position detection unit connected to the main body to transmit and receive with the first position detection unit.

The second position detection unit may include a field generator configured to generate a magnetic field in the vicinity of the ultrasonic probe, and the first position detection unit may include a sensor unit disposed inside the sound absorbing member to detect the magnetic field generated from the field generator.

The first position detecting unit may include a field generator configured to generate a magnetic field inside the ultrasonic probe, and the second position detection unit may include a sensor unit disposed inside the sound absorbing member to detect the magnetic field generated from the field generator.

Advantageous Effects

The present disclosure can improve the stability of a biopsy by further accurately measuring a position and movement distance of a needle.

The present disclosure can secure an inner space of a case by arranging a sensor unit that detects a magnetic field of a magnetized needle inside a transducer, thereby improving the degree of freedom in the design of the case.

The present disclosure can reduce the number of substrates by integrating a ground substrate, a signal substrate, or a sensor substrate as one substrate, thereby simplifying a manufacturing process and reducing a manufacturing cost.

MODE OF THE DISCLOSURE

The embodiments described in the present specification and the configurations shown in the drawings are only examples of preferred embodiments of the present disclosure, and various modifications may be made at the time of filing of the present disclosure to replace the embodiments and drawings of the present specification.

Like reference numbers or signs in the various drawings of the application represent parts or components that perform substantially the same functions.

The terms used herein are for the purpose of describing the embodiments and are not intended to restrict and/or to limit the present disclosure. For example, the singular expressions herein may include plural expressions, unless the context clearly dictates otherwise.

Also, the terms "comprises" and "has" are intended to indicate that there are features, numbers, steps, operations, elements, parts, or combinations thereof described in the specification, and do not exclude the presence or addition of one or more other features, numbers, steps, operations, elements, parts, or combinations thereof.

It will be understood that, although the terms first, second, etc. may be used herein to describe various components, these components should not be limited by these terms, and these terms are only used to distinguish one component from another.

For example, without departing from the scope of the present disclosure, the first component may be referred to as a second component, and similarly, the second component may also be referred to as a first component.

The term "and/or" includes any combination of a plurality of related items or any one of a plurality of related items.

In this specification, the terms "front end," "rear end," "upper portion," "lower portion," "upper end" and "lower end" used in the following description are defined with reference to the drawings, and the shape and position of each component are not limited by these terms.

Hereinafter, embodiments of the present disclosure will be described in detail with reference to the accompanying drawings.

Figure 1:
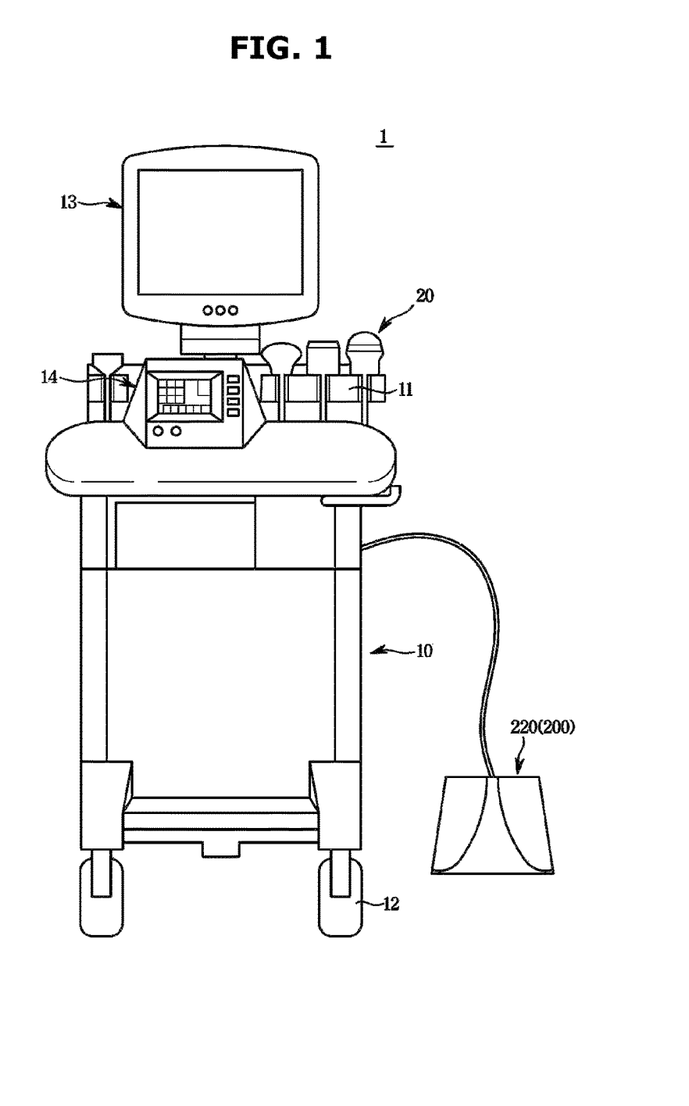
FIG. 1 is a view illustrating an ultrasonic imaging apparatus including an ultrasonic probe according to the present disclosure.

FIG. 1 is a view illustrating an ultrasonic imaging apparatus including an ultrasonic probe according to the present disclosure.

As illustrated in FIG. 1, an ultrasonic imaging apparatus 1 according to the present disclosure is a main body 10, and an ultrasonic probe 20 configured to transmit an ultrasonic signal to an object to be diagnosed and receive a signal reflected from the object.

In order to obtain an ultrasonic image of an object, the ultrasonic probe 20 may transmit an ultrasonic signal to the object and may receive an ultrasonic signal reflected from the object and transmit the reflected ultrasonic signal to a controller (not shown). The ultrasonic probe 20 may be connected to the main body 10 by a cable.

The main body 10 may be provided with a display 13 to display a diagnosis result obtained through the received ultrasonic signal. An application related to the operation of the ultrasonic imaging apparatus 1 may be displayed on the display 13.

For example, the display 13 may display an ultrasonic image obtained during an ultrasonic diagnosis process or matters related to the operation of the ultrasonic imaging apparatus 1.

The display 13 may be implemented as a cathode ray tube (CRT), a liquid crystal display (LCD), or the like. A plurality of the displays 13 may be provided. When the plurality of displays 13 is provided, the displays 13 may include a main display and a sub-display.

For example, an ultrasonic image obtained during the ultrasonic diagnosis process may be displayed on the main display, and matters related to the operation of the ultrasonic imaging apparatus 1 may be displayed on the sub-display.

The main body 10 may be provided with an input device 14. The input device 14 may be provided in the form of a keyboard, a foot switch, or a foot pedal.

When the input device 14 is a keyboard, the keyboard may be provided at an upper portion of the main body 10. When the input device 14 is a foot switch or a foot pedal, the foot switch or the foot pedal may be provided at a lower portion of the main body 10. A user may control the operation of the ultrasonic imaging apparatus 1 through the input device 14.

The ultrasonic probe 20 may be placed on the main body 10 by a holder 11. When the ultrasonic imaging apparatus 1 is not used, the user may place and store the ultrasonic probe 20 on the holder 11.

The main body 10 may be provided with a moving device 12 to move the ultrasonic imaging apparatus 1. The moving device 12 may be a plurality of casters provided on a bottom surface of the main body 10.

The plurality of casters may be aligned to allow the main body 10 to travel in a specific direction, may be arranged to allow the main body 10 to freely move, or may be locked to allow the main body 10 to stop at a specific position.

Figure 2:
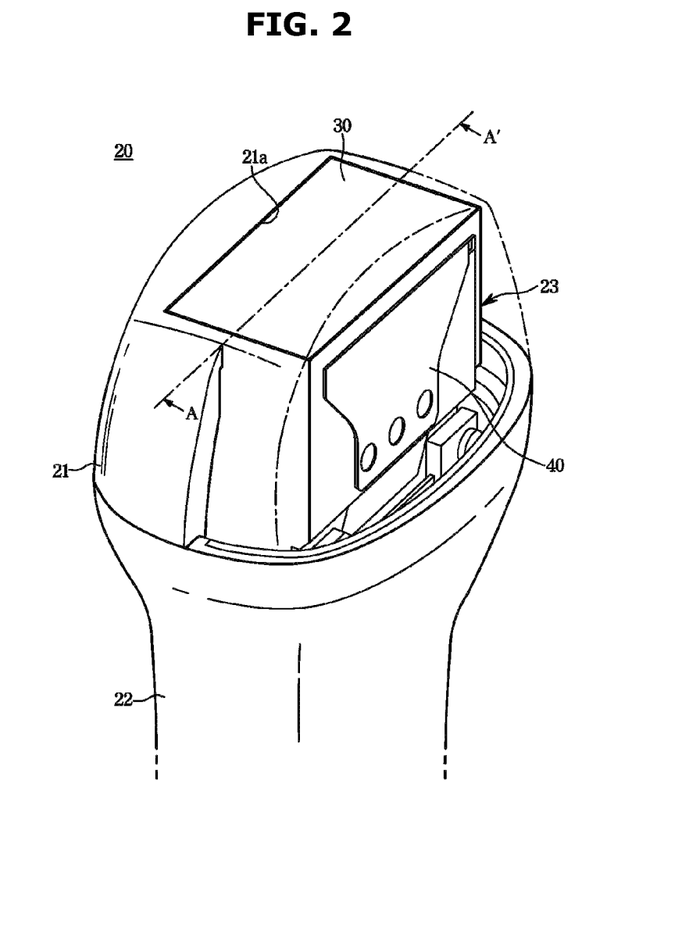
FIG. 2 is a view schematically illustrating the inside of the ultrasonic probe according to the present disclosure.
Figure 3:
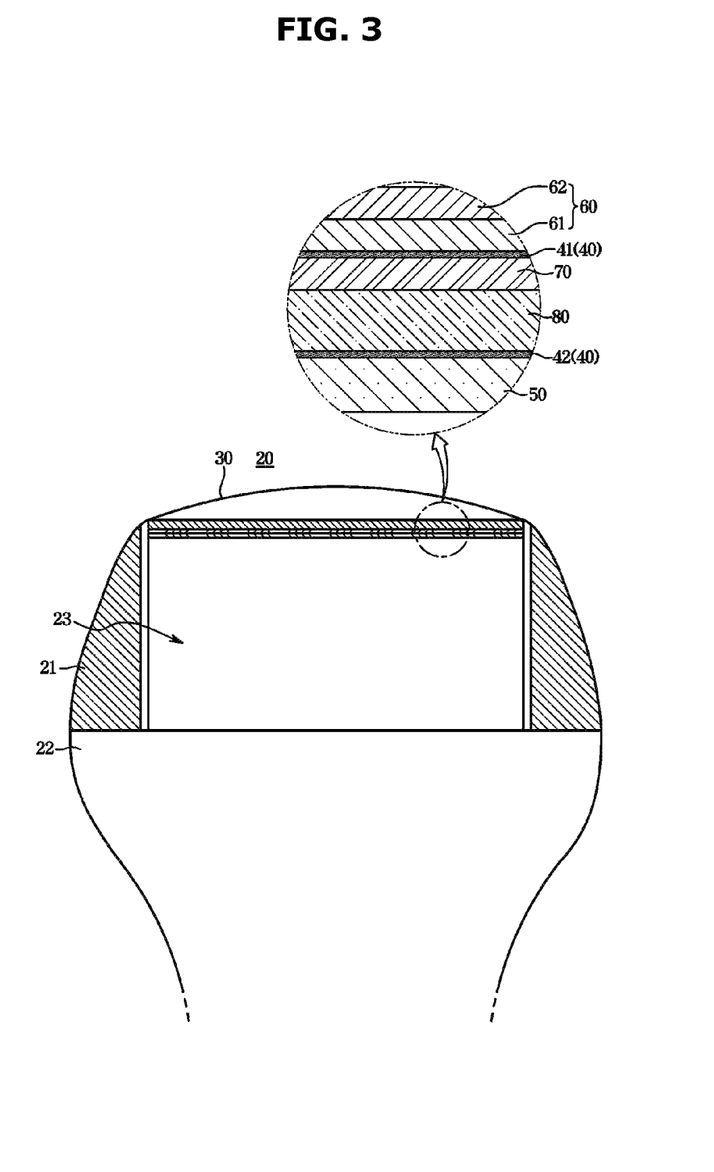
FIG. 3 is an enlarged view illustrating a part of section A-A" of the ultrasonic probe according to the present disclosure illustrated in FIG. 2.

FIG. 2 is a view schematically illustrating the inside of the ultrasonic probe according to the present disclosure. FIG. 3 is an enlarged view illustrating a part of section A-A" of the ultrasonic probe according to the present disclosure illustrated in FIG. 2.

As illustrated in FIGS. 2 and 3, the ultrasonic probe 20 according to the present disclosure may include a transducer 23 to generate an ultrasonic signal.

The ultrasonic probe 20 may include a lens 30 provided to transmit an ultrasonic signal generated from the transducer 23 to the outside. The lens 30 may focus an ultrasonic signal.

The lens 30 may be made of a material such as silicone and rubber having an acoustic impedance value similar to that of the object. The lens 30 may be provided in a convex type in which a central portion has a convex curved surface, or may be provided in a linear type having a flat surface.

The ultrasonic probe 20 may include a case 21 in which the transducer 23 is accommodated and having an opening 21a on one side such that the lens 30 is in contact with an external object, and a handle 22 mounted on the other side of the case 21.

The transducer 23 may include a piezoelectric layer 70, a matching layer 60 disposed in the front of the piezoelectric layer 70, and a sound absorbing layer 50 disposed in the rear of the piezoelectric layer 70.

In general, the transducer 23 may include a magnetostrictive ultrasonic transducer using the magnetostrictive effect of a magnetic body, a capacitive micromachined ultrasonic transducer that transmits and receives ultrasonic waves using vibrations of hundreds or thousands of finely processed thin films, or a piezoelectric ultrasonic transducer using the piezoelectric effect of a piezoelectric material.

Hereinafter, the piezoelectric ultrasonic transducer will be described as an example of the transducer 23 according to the present disclosure.

Effects of generating a voltage when a mechanical pressure is applied to a predetermined material and causing a mechanical deformation when a voltage is applied are referred to as a piezoelectric effect and an inverse piezoelectric effect, respectively, and a material having these effects may be referred to as a piezoelectric material.

That is, the piezoelectric material may include a material that converts electrical energy into mechanical vibration energy and mechanical vibration energy into electrical energy.

The transducer 23 according to the present disclosure may include the piezoelectric layer 70 made of a piezoelectric material generating ultrasonic waves by converting an electrical signal into mechanical vibration, and an acoustic layer 80 disposed in the rear of the piezoelectric layer 70.

The piezoelectric layer 70, which is configured to generate ultrasonic waves using a resonance phenomenon, may be formed of a ceramic of lead zirconate titanate (PZT), a PZNT single crystal made of a solid solution of lead zinc niobate and lead titanate, a PZMT single crystal made of a solid solution of lead magnesium niobate and lead titanate, or the like.

By forming the piezoelectric layer 70 as a single crystal, the ultrasonic probe 20 having a wide bandwidth may be formed, and ultrasonic signals in a high frequency region as well as a low frequency region may be transmitted and received.

In addition, after the transducer 23 is channel-divided, a process of making a curvature of the divided transducer 23 may be easily performed, and accordingly, the shape of the ultrasonic probe 20 may not be limited.

The piezoelectric layer 70 may be provided in the form of a kerf to maximize ultrasonic generation performance. However, the present disclosure is not limited thereto.

The acoustic layer 80 may be provided to have an acoustic impedance higher than that of the piezoelectric layer 70. The acoustic layer 80 may be made of a material having electrical conductivity. A thickness of the acoustic layer 80 may be provided as ½, ¼, ⅛ or 1/16 of a wavelength of the piezoelectric material constituting the piezoelectric layer 70. However, the present disclosure is not limited thereto.

The acoustic layer 80 may include an acoustic reflector. The acoustic reflector may be disposed in the front of the sound absorbing layer 50. The acoustic layer 80 may totally reflect ultrasonic waves traveling to the sound absorbing layer 50. Through this configuration, the bandwidth of the ultrasonic probe 20 may be increased and the sensitivity thereof may be increased.

The acoustic layer 80 may be made of a material having a very high acoustic impedance to totally reflect ultrasonic waves. For example, the acoustic layer 80 may be formed of at least one of tungsten carbide and graphite composite materials.

Substrates 40 to which an electrical signal may be applied may be formed on front and rear surfaces of the piezoelectric layer 70, respectively. The substrate 40 may include a ground substrate 41 formed in the front of the piezoelectric layer 70 and a signal substrate 42 formed in the rear of the piezoelectric layer 70.

The substrate 40 including the ground electrode 41 and the signal electrode 42 may be formed of a flexible printed circuit board (FPCB).

The transducer 23 may include an electrode (not shown). For example, an electrode electrically connected to the signal substrate 42 may be provided on the rear surface of the piezoelectric layer 70, and an electrode electrically connected to the ground substrate 41 may be provided on the front surface of the piezoelectric layer 70.

However, the present disclosure is not limited thereto, an electrode formed on the front surface of the piezoelectric layer 70 may be electrically connected to the signal substrate 42, and an electrode formed on the rear surface of the piezoelectric layer 70 may be electrically connected to the ground substrate 41.

The transducer 23 may include the matching layer 60. The matching layer 60 may serve to reduce a difference in acoustic impedance between the piezoelectric layer 70 and an object so that ultrasonic waves generated from the piezoelectric layer 70 are maximally transmitted to the object.

The matching layer 60 may reduce the difference in acoustic impedance between the piezoelectric layer 70 and the object to match the acoustic impedances of the piezoelectric layer 70 and the object so that the ultrasonic waves generated in the piezoelectric layer 70 may be efficiently transmitted to the object.

The matching layer 60 may be disposed adjacent to the piezoelectric layer 70. The matching layer 60 may be located in the front of the piezoelectric layer 70. The matching layer 60 may be provided to have an intermediate value between the acoustic impedance of the piezoelectric layer 70 and the acoustic impedance of the object and may be formed of a glass or resin material.

A plurality of the matching layers 60 having different materials may be provided to be stacked such that the acoustic impedance of the matching layer 60 may gradually change from the piezoelectric layer 70 toward the object.

The matching layer 60 may include a first matching layer 61 and a second matching layer 62. The plurality of matching layers 60 may be made of different materials.

The transducer 23 may include the sound absorbing layer 50. The sound absorbing layer 50 may be disposed adjacent to the piezoelectric layer 70. The sound absorbing layer 50 may be located in the rear of the piezoelectric layer 70.

The sound absorbing layer 50 may reduce pulse widths of ultrasonic waves by suppressing free vibrations of the piezoelectric layer 70 and may prevent ultrasonic images from being distorted by blocking unnecessary propagation of the ultrasonic waves to the rear of the piezoelectric layer 70.

The sound absorbing layer 50 may be formed of a material including rubber to which an epoxy resin, tungsten powder, and the like are added.

Figure 4:
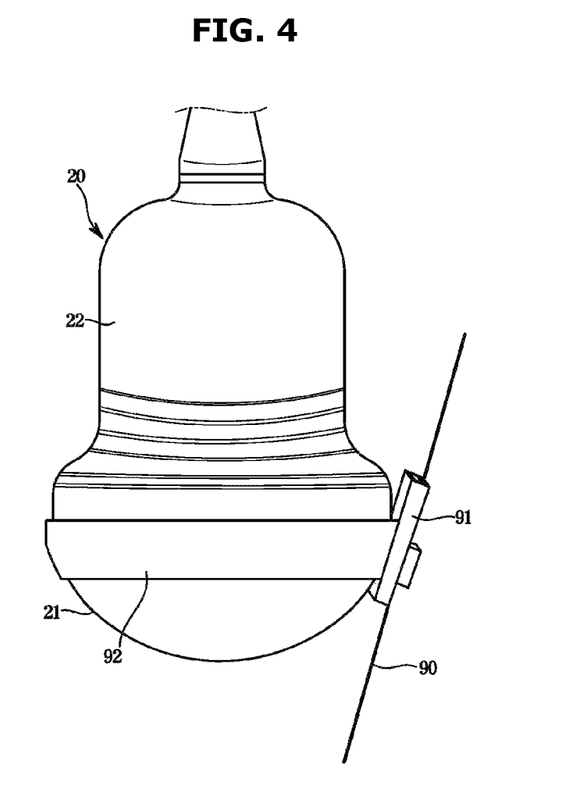
FIG. 4 is a view illustrating a needle in the ultrasonic probe according to the present disclosure.
Figure 5:
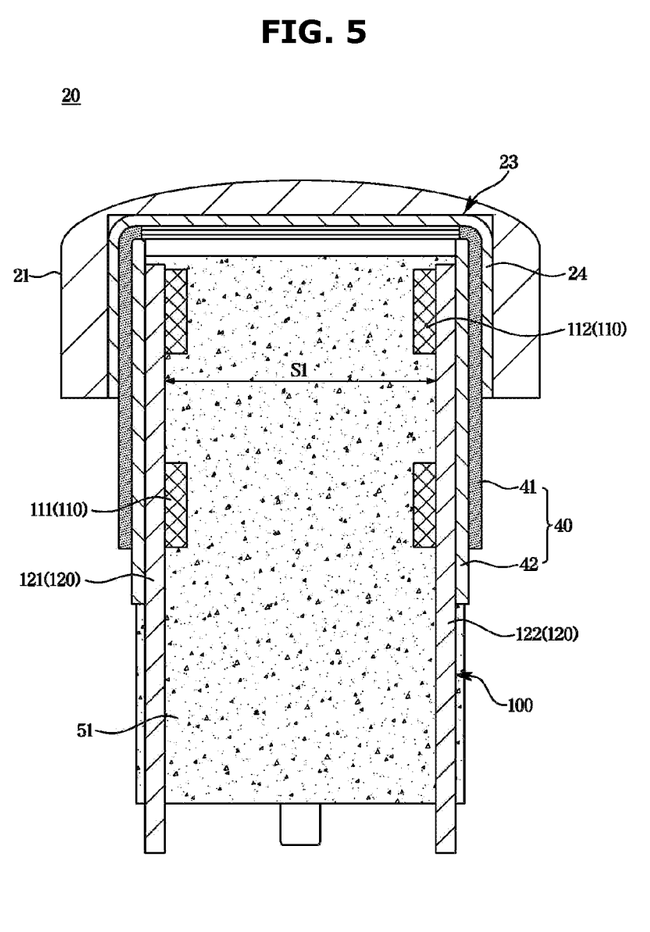
FIG. 5 is a view illustrating a sensor unit disposed inside a transducer in the ultrasonic probe according to a first embodiment of the present disclosure.

FIG. 4 is a view illustrating a needle in the ultrasonic probe according to the present disclosure. FIG. 5 is a view illustrating a sensor unit disposed inside a transducer in the ultrasonic probe according to a first embodiment of the present disclosure.

As illustrated in FIGS. 4 and 5, the ultrasonic probe 20 according to the present disclosure may include a biopsy needle 90 inserted into an object in the vicinity of the case 21, and a biopsy needle guide 91 detachably mounted on the case 21 to guide the biopsy needle 90.

However, the present disclosure is not limited thereto, and the biopsy needle guide 91 may be detachably mounted to the handle 22 or may be detachably mounted to the case 21 and the handle 22.

The biopsy needle guide 91 may include a mounting member 92 provided to be detachably mounted to the case 21 or the handle 22. The mounting member 92 may include a rubber band having an elastic material. The mounting member 92 may surround the case 21 or the handle 22.

However, the present disclosure is not limited thereto, and the mounting member 92 may be configured to be flexible, such as a bracket made of plastic or the like, and may be variously provided within a limit in which the mounting member 92 may be firmly fastened to the ultrasonic probe 20 having various sizes and shapes.

The biopsy needle 90 may be a medical needle inserted into an object, for example, into a lesioned site inside the object through a hole in s human body, and used for treatment or biopsy. The biopsy needle 90 may be implemented as, for example, a clear track or a virtual track.

The transducer 23 according to the present disclosure may include a sensor unit 100 provided to measure a position of the biopsy needle 90.

The biopsy needle 90 may be magnetized, and the sensor unit 100 may be configured to detect a magnetic field generated by the magnetized biopsy needle 90. The sensor unit 100 may include a sensor 110 provided to detect the position of the localized biopsy needle 90. A plurality of the sensors 110 may be provided.

The magnetized biopsy needle 90 may form a magnetic field in an area of a predetermined range. The sensor unit 100 may sense a magnetic field from the biopsy needle 90, along with an earth's magnetic field and any other background magnetic field.

The ultrasonic imaging apparatus 1 (see FIG. 1) may determine a direction and position of the biopsy needle 90 related to the transducer 23 from the field detected by the sensor unit 100. Accordingly, the magnetically detected position of the biopsy needle 90 may be displayed on the display 13 (see FIG. 1) together with an ultrasonic image.

Because the user may easily grasp a moving distance of the biopsy needle 90 through the display 13 or the like, work such as collecting an object may be performed more safely.

The sensor unit 100 according to the present disclosure may be disposed inside the transducer 23. The sensor unit 100 may be disposed inside a sound absorbing member 51.

As the sensor unit 100 according to the present disclosure may be disposed inside the transducer 23, a space inside the transducer 23 may be secured, and a separate mounting case for mounting the sensor unit 100 to the outside of the transducer 23 may not be required, so that a manufacturing cost of the ultrasonic probe 20 may be reduced.

The transducer 23 may include the substrate 40 including the ground substrate 41 disposed on one side of the piezoelectric layer 70 (see FIG. 3) and the signal substrate 42 disposed on the other side of the piezoelectric layer 70 to be disposed at the inner side of the ground substrate 41.

The sensor unit 100 of the transducer 23 according to a first embodiment of the present disclosure may include a sensor substrate 120 on which the sensor 110 is detachably mounted. The sensor substrate 120 may be disposed at an inner side of the signal substrate 42.

The transducer 23 may include the sound absorbing member 51 disposed on one side of the sound absorbing layer 50, and the sensor substrate 120 may be disposed between the sound absorbing member 51 and the signal substrate 42. The signal substrate 42 may be disposed between the sensor substrate 120 and the ground substrate 41.

A plurality of the sensor substrates 120 may be provided. The sensor substrate 120 may include a first sensor substrate 121 provided on one side of the inside of the sound absorbing member 51, and a second sensor substrate 122 provided on the other side of the inside of the sound absorbing member 51 to be spaced apart from the first sensor substrate 121.

A distance S1 by which the first sensor substrate 121 and the second sensor substrate 122 are spaced apart from each other may be 10 to 60 times an acoustic wavelength of the transducer 23. However, the present disclosure is not limited thereto.

The sensor 110 may include a first sensor 111 mounted on the first sensor substrate 121 and a second sensor 112 mounted on the second sensor substrate 122. A plurality of the first sensors 111 may be provided to be spaced apart from each other on the first sensor substrate 121, and the plurality of the second sensors 112 may be provided to be spaced apart from each other on the second sensor substrate 122. However, the present disclosure is not limited thereto.

The first sensor 111 and the second sensor 112 may face each other.

The transducer 23 may include a cover member 24 provided to cover the outside of the transducer 23. The cover member 24 may include a CS film. As the sensor unit 100 is disposed inside the transducer 23, the sensor unit 100 may be covered together by the cover member 24.

The ultrasonic probe 20 may include a lens 30 provided to transmit an ultrasonic signal generated from the transducer 23 to the outside, and therefore, the transducer 23 according to the present disclosure may prevent a disinfectant for disinfecting the lens 30 (see FIG. 3) from penetrating into the sensor unit 100.

In the transducer 23 according to the present disclosure, as the sensor unit 100 is disposed inside the transducer 23 instead of outside, the lens 30 and the case 21 may be combined by a molding process.

Unlike combining the lens 30 and the case 21 by an adhesive method using an adhesive or the like, as the lens 30 and the case 21 are combined by the molding process, a manufacturing process of the ultrasonic probe 20 may be simplified, and risk of defect may be reduced.

The transducer 23 may include the acoustic layer 80 (see FIG. 3) having a non-magnetic material to prevent interference with the reception of the magnetic field of the sensor unit 100. Accordingly, even when the sensor unit 100 is disposed inside the transducer 23, the reception of the magnetic field of the biopsy needle 90 by the sensor unit 100 may be not hindered by the acoustic layer 80.

Figure 6:
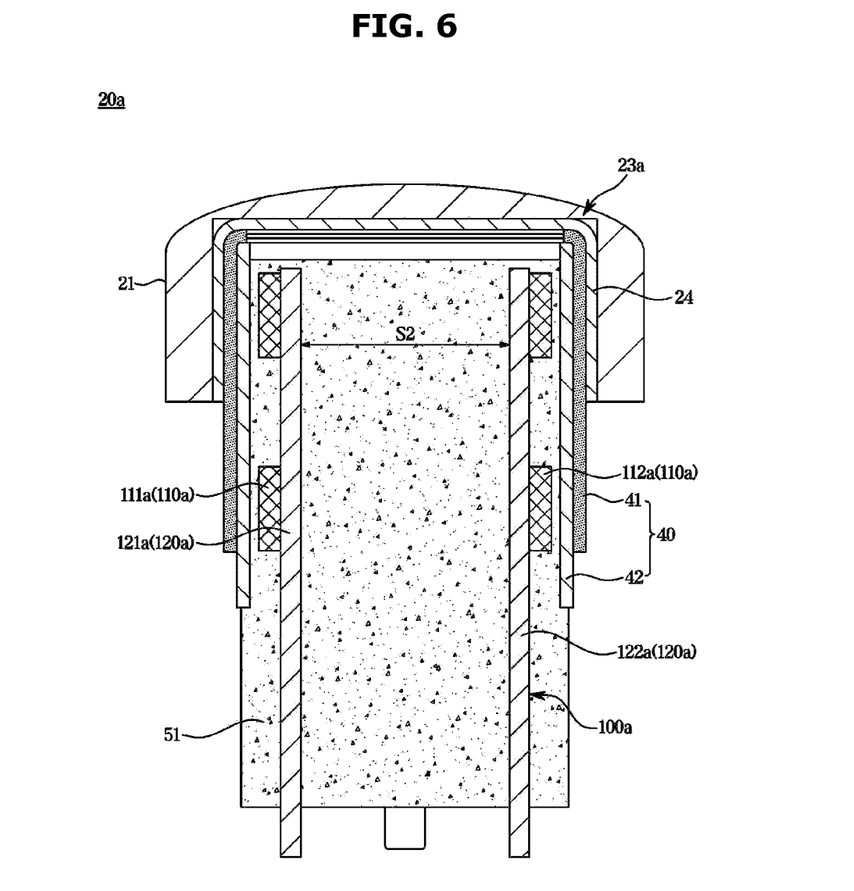
FIG. 6 is a view illustrating a sensor unit disposed inside a transducer in an ultrasonic probe according to a second embodiment of the present disclosure.

FIG. 6 is a view illustrating a sensor unit disposed inside a transducer in an ultrasonic probe according to a second embodiment of the present disclosure. As illustrated in FIG. 6, a sensor unit 100a according to a second embodiment of the present disclosure may be disposed inside a transducer 23a. The sensor unit 100a may be disposed inside the sound absorbing member 51.

Hereinafter, the sensor unit 100a according to the second embodiment will be described with a focus on differences from the sensor unit 100 according to the first embodiment (see FIG. 5).

The transducer 23a according to the second embodiment of the present disclosure may include the ground substrate 41 disposed on one side of the piezoelectric layer 70 (see FIG. 3), and the signal substrate 42 disposed on the other side of the piezoelectric layer 70 to be disposed at an inner side of the ground substrate 41.

The sensor unit 100a according to the second embodiment of the present disclosure may include a sensor substrate 120a on which a sensor 110a is detachably mounted. The sensor substrate 120a may be disposed at the inner side of the signal substrate 42.

The sensor substrate 120a may be disposed between the sound absorbing member 51 and the signal substrate 42. The signal substrate 42 may be disposed between the sensor substrate 120a and the ground substrate 41.

A plurality of the sensor substrates 120a may be provided. The sensor substrate 120a may include a first sensor substrate 121a provided on one side of the inside of the sound absorbing member 51, and a second sensor substrate 122a provided on the other side of the inside of the sound absorbing member 51 to be spaced apart from the first sensor substrate 121a.

A distance S2 by which the first sensor substrate 121a and the second sensor substrate 122a according to the second embodiment of the present disclosure are spaced apart from each other may be smaller than the distance S1 (see FIG. 5) by which the first sensor substrate 121 and the second sensor substrate 122 according to the first embodiment of the present disclosure are spaced apart from each other.

The sensor 110a may include a first sensor 111a mounted on the first sensor substrate 121a and a second sensor 112a mounted on the second sensor substrate 122a.

The first sensor 111a and the second sensor 112a may be disposed adjacent to an inner surface of the sound absorbing member 51 to face the signal substrate 42. The sensor 110a may be mounted on the sensor substrate 120*a* to be disposed between the sensor substrate 120*a* and the signal substrate 42.

The transducer 23*a* may include the cover member 24 provided to cover the outside of the transducer 23*a*. The cover member 24 may include the CS film. As the sensor unit 100*a* is disposed inside the transducer 23*a*, the sensor unit 100*a* may be covered together by the cover member 24.

Figure 7:
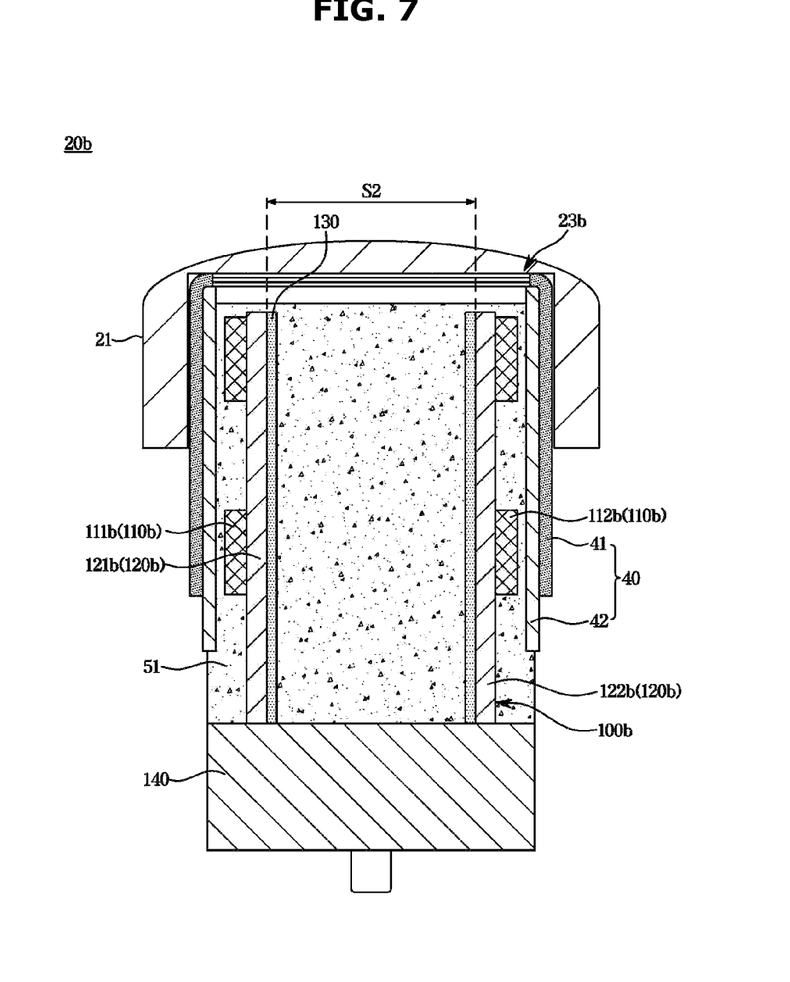
FIG. 7 is a view illustrating a sensor unit disposed inside a transducer in an ultrasonic probe according to a third embodiment of the present disclosure.

FIG. 7 is a view illustrating a sensor unit disposed inside a transducer in an ultrasonic probe according to a third embodiment of the present disclosure. As illustrated in FIG. 7, a sensor unit 100*b* according to a third embodiment of the present disclosure may be disposed inside a transducer 23*b*. The sensor unit 100*b* may be disposed inside the sound absorbing member 51.

Hereinafter, the sensor unit 100*b* according to the third embodiment will be described with a focus on differences from the sensor unit 100*a* according to the second embodiment (see FIG. 6).

The transducer 23*b* according to the third embodiment of the present disclosure may include the substrate 40 including the ground substrate 41 disposed on one side of the piezoelectric layer 70 (see FIG. 3) and the signal substrate 42 disposed on the other side of the piezoelectric layer 70 to be disposed at the inner side of the ground substrate 41.

The sensor unit 100*b* according to according to the third embodiment of the present disclosure may include a sensor substrate 120*b* on which a sensor 110*b* is detachably mounted. The sensor substrate 120*b* may be disposed at the inner side of the signal substrate 42.

The sensor substrate 120*b* may be disposed between the sound absorbing member 51 and the sensor 110*b*. The signal substrate 42 may be disposed between the sensor 110*b* and the ground substrate 41.

A plurality of the sensor substrates 120*b* may be provided. The sensor substrate 120*b* may include a first sensor substrate 121*b* provided on one side of the inside of the sound absorbing member 51, and a second sensor substrate 122*b* provided on the other side of the inside of the sound absorbing member 51 to be spaced apart from the first sensor substrate 121*b*.

The distance S2 by which the first sensor substrate 121*b* and the second sensor substrate 122*b* according to the third embodiment of the present disclosure are spaced apart from each other may be equal to the distance S2 by which the first sensor substrate 121*a* and the second sensor substrate 122*a* according to the second embodiment of the present disclosure are spaced apart from each other. However, the present disclosure is not limited thereto.

The sensor 110*b* may include a first sensor 111*b* mounted on the first sensor substrate 121*b* and a second sensor 112*b* mounted on the second sensor substrate 122*b*.

The first sensor 111*b* and the second sensor 112*b* may be disposed adjacent to the inner surface of the sound absorbing member 51 to face the signal substrate 42. The sensor 110*b* may be mounted on the sensor substrate 120*b* to be disposed between the sensor substrate 120*b* and the signal substrate 42.

The sensor unit 100*b* according to the third embodiment of the present disclosure may include a heat radiation sheet 130 disposed on an inner surface of the sensor substrate 120*b*. The heat radiation sheet 130 may be in contact with the sensor substrate 120*b* to be disposed between the sound absorbing member 51 and the sensor substrate 120*b*. The heat radiation sheet 130 may be disposed on the inner surface of the sensor substrate 120*b*.

The sensor unit 100*b* may include a stabilizer 140 connected to the heat radiation sheet 130 so that the heat radiation sheet 130 radiates heat from the sensor 110*b*. The stabilizer 140 may be disposed at one end of the sound absorbing member 51. The stabilizer 140 may be disposed at a lower end of the sound absorbing member 51. However, the present disclosure is not limited thereto.

As the transducer 23*b* according to the third embodiment includes the heat radiation sheet 130 in contact with the sensor substrate 120*b* and the stabilizer 140 connected to the heat radiation sheet 130, heat generated from the sensor 110*b* may be radiated.

Figure 8:
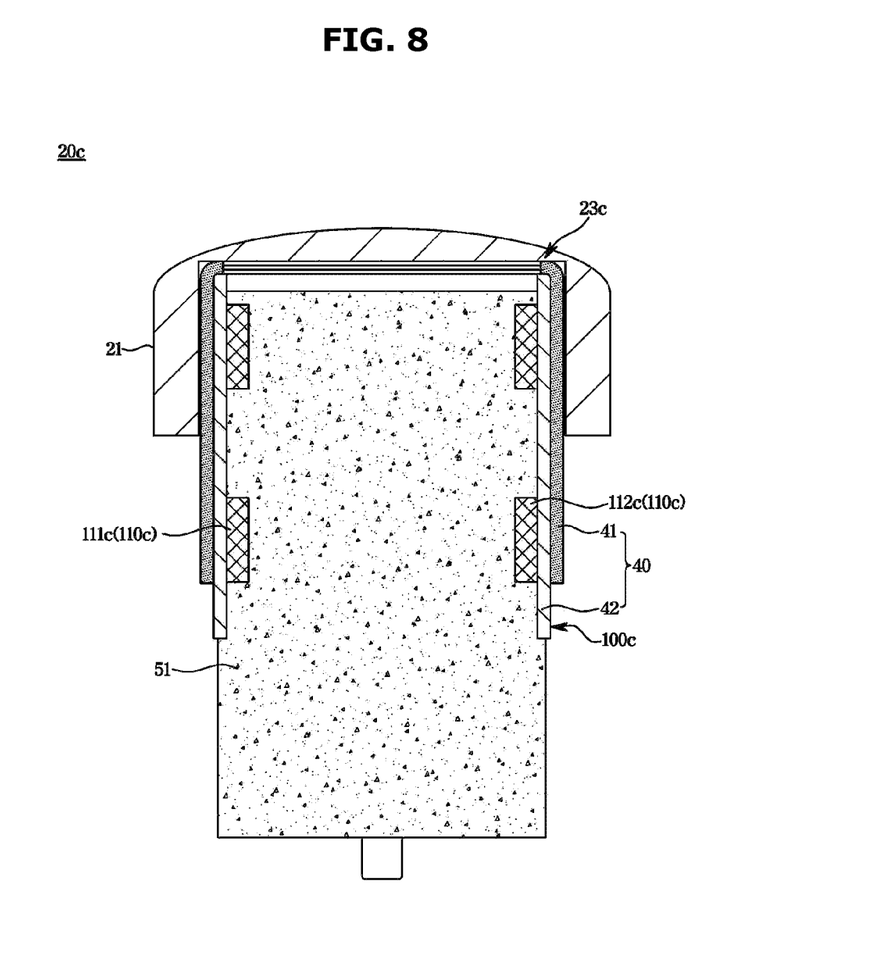
FIG. 8 is a view illustrating a sensor unit disposed inside a transducer in an ultrasonic probe according to a fourth embodiment of the present disclosure.

FIG. 8 is a view illustrating a sensor unit disposed inside a transducer in an ultrasonic probe according to a fourth embodiment of the present disclosure. As illustrated in FIG. 8, a sensor unit 100*c* according to a fourth embodiment of the present disclosure may be disposed inside a transducer 23*c*. The sensor unit 100*c* may be disposed inside the sound absorbing member 51.

Hereinafter, the sensor unit 100*c* according to the fourth embodiment will be described with a focus on differences from the sensor unit 100 according to the first embodiment (see FIG. 5).

The transducer 23*c* according to the fourth embodiment of the present disclosure may include the substrate 40 including the ground substrate 41 disposed on one side of the piezoelectric layer 70 (see FIG. 3) and the signal substrate 42 disposed on the other side of the piezoelectric layer 70 to be disposed at the inner side of the ground substrate 41. A sensor 110*c* may be detachably mounted on the signal substrate 42.

The sensor 110*c* may include a first sensor 111*c* mounted on the signal substrate 42 disposed on one side of the inside of the sound absorbing member 51 and a second sensor 112*c* mounted on the signal substrate 42 disposed on the other side of the inside of the sound absorbing member 51.

A plurality of the sensors 110*c* may be provided to be spaced apart from each other on the signal substrate 42. However, the present disclosure is not limited thereto.

The first sensor 111*c* and the second sensor 112*c* may face each other. The sensor 110*c* may be mounted on the signal substrate 42 to be disposed between the sound absorbing member 51 and the signal substrate 42. The sensor 110*c* may be detachably mounted on the inner surface of the signal substrate 42.

In the transducer 23*c* according to the fourth embodiment of the present disclosure, as the sensor 110*c* is mounted on the signal substrate 42, unlike the transducer 23 according to the first embodiment of the present disclosure, the separate sensor substrate 120 (see FIG. 5) for mounting the sensor 110*c* may not be required, so that the number of the substrates 40 may be reduced, and a manufacturing cost of an ultrasonic probe 20*c* may be reduced.

Therefore, the signal substrate 42 according to the fourth embodiment of the present disclosure may perform together the functions of the signal substrate 42 and the sensor substrate 120 (see FIG. 5) according to the first embodiment of the present disclosure.

Figure 9:
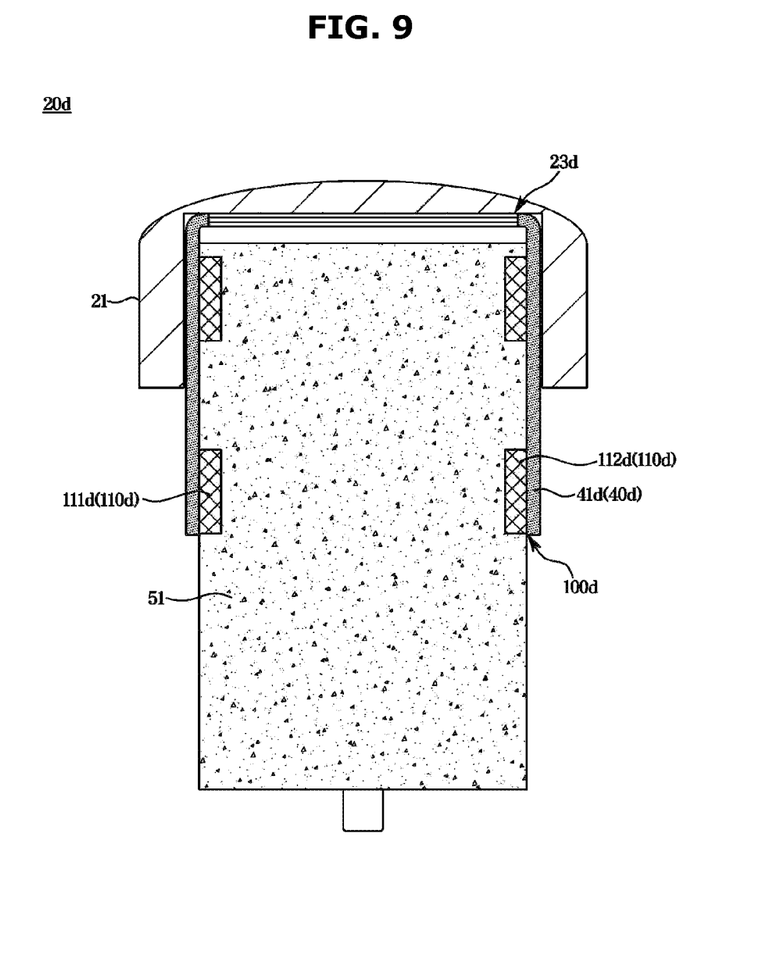
FIG. 9 is a view illustrating a sensor unit disposed inside a transducer in an ultrasonic probe according to a fifth embodiment of the present disclosure.

FIG. 9 is a view illustrating a sensor unit disposed inside a transducer in an ultrasonic probe according to a fifth embodiment of the present disclosure. As illustrated in FIG. 9, a sensor unit 100*d* according to a fifth embodiment of the present disclosure may be disposed inside a transducer 23*d*. The sensor unit 100*d* may be disposed inside the sound absorbing member 51.

Hereinafter, the sensor unit 100d according to the fifth embodiment will be described with a focus on differences from the sensor unit 100d according to the fourth embodiment (see FIG. 8).

The transducer 23d according to the fifth embodiment of the present disclosure may include a substrate 40d including a ground substrate 41d disposed on one side of the piezoelectric layer 70 (see FIG. 3). A sensor 110d may be detachably mounted on the ground substrate 41d.

The sensor 110d may include a first sensor 111d mounted on the ground substrate 41d disposed on one side of the inside of the sound absorbing member 51 and a second sensor 112d mounted on the ground substrate 41d disposed on the other side of the inside of the sound absorbing member 51.

A plurality of the sensors 110d may be provided to be spaced apart from each other on the ground substrate 41d. However, the present disclosure is not limited thereto.

The first sensor 111d and the second sensor 112d may face each other. The sensor 110d may be mounted on the ground substrate 41d to be disposed between the sound absorbing member 51 and the ground substrate 41d. The sensor 110d may be detachably mounted on an inner surface of the ground substrate 41d.

In the transducer 23d according to the fifth embodiment of the present disclosure, as the sensor 110d is mounted on the ground substrate 41d, unlike the transducer 23c (see FIG. 8) according to the fourth embodiment of the present disclosure, the separate signal substrate 42 (see FIG. 8) for mounting the sensor 110d may not be required, so that the number of the substrates 40d may be further reduced, and a manufacturing cost of an ultrasonic probe 20d may be reduced.

Therefore, the ground substrate 41d according to the fifth embodiment of the present disclosure may perform together the functions of the signal substrate 42 and the ground substrate 41 according to the first embodiment of the present disclosure.

Figure 10:
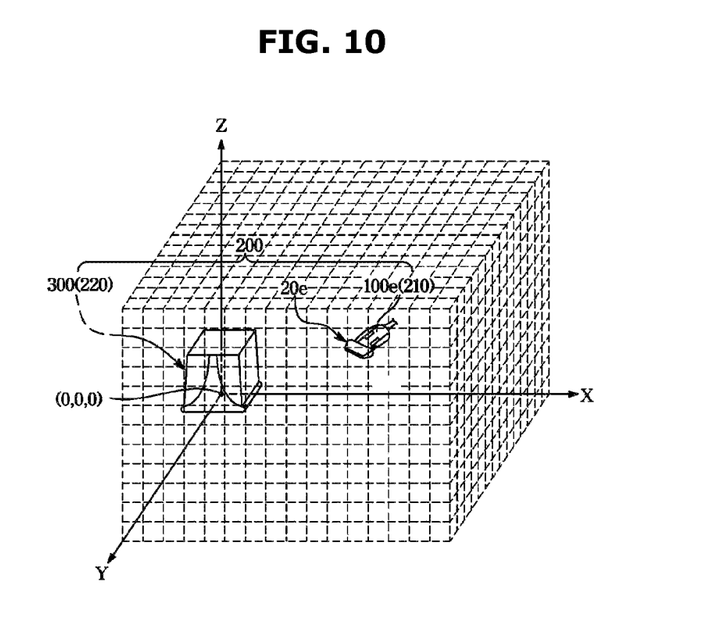
FIG. 10 is a diagram illustrating transmission/reception between an ultrasonic probe and a position detection unit according to a sixth embodiment of the present disclosure.

FIG. 10 is a diagram illustrating transmission/reception between an ultrasonic probe and a position detection unit according to a sixth embodiment of the present disclosure. As illustrated in FIG. 10, an ultrasonic probe 20e according to a sixth embodiment of the present disclosure may include a position detection unit 200.

The position detection unit 200 may include a first position detection unit 210 including a sensor unit 100e disposed inside the ultrasonic probe 20e. The sensor unit 100e according to the sixth embodiment of the present disclosure may be the same as the sensor unit 100 (see FIG. 5) according to the first embodiment of the present disclosure.

The position detection unit 200 may include a second position detection unit 220 connected to the ultrasonic imaging apparatus 1 (see FIG. 1). The second position detection unit 220 may include a field generator 300 to generate a magnetic field.

That is, the first position detection unit 210 may include the sensor unit 100e, and the second position detection unit 220 may include the field generator 300 to generate a magnetic field like the magnetized biopsy needle 90 (see FIG. 4) according to the first embodiment of the present disclosure.

Therefore, the ultrasonic probe 20e according to the sixth embodiment of the present disclosure may detect a position of the ultrasonic probe 20e through the sensor unit 100e and the field generator 300.

In general, an ultrasonic image acquired through the ultrasonic imaging apparatus 1 may be registered with a medical image acquired from another medical imaging apparatus. The image registration may correspond to a processing technique of displaying different images in one coordinate system by transforming the different images.

The image registration may refer to reconstructing two or more images into a single composite image, and the user may grasp how different images correspond to each other by using an image registration technique.

In the field of diagnosis using a medical image, the image registration technique may be used in order to compare images of an affected area over time or with an image of a normal tissue.

In addition, in order to use an image, in which advantages or disadvantages of different image acquisition modalities are complemented, for diagnosis, the image registration technique that may allow the acquired images to be displayed and compared in the same space may be used.

For such the medical image registration, the position detection unit 200 that acquires position information of the ultrasonic probe 20e may be used, and the first position detection unit 210 may be mounted on the ultrasonic probe 20e to detect the position of the ultrasonic probe 20e to acquire the position information for image registration.

Accordingly, the second position detection unit 220 including the field generator 300 according to the sixth embodiment of the present disclosure may be provided outside the ultrasonic imaging apparatus 1, and may be physically coupled to the ultrasonic imaging apparatus 1 by being connected to a cable or the like.

The field generator 300 serves as a reference point for determining coordinate information of the first position detection unit 210 including the sensor unit 100e, and it may be determined at which coordinates the sensor unit 100e is located in a space based on the field generator 300.

That is, the field generator 300 may generate a magnetic field within a predetermined range from a region in which the sensor unit 100e is located. The sensor unit 100e may detect the magnetic field formed by the field generator 300, and may provide the position information detected in a three-dimensional space to the ultrasonic imaging apparatus 1.

However, the present disclosure is not limited thereto, the first position detection unit 210 disposed inside the ultrasonic probe 20e may include the field generator 300, and the second position detection unit 220 disposed outside the ultrasonic imaging apparatus 1 may include the sensor unit 100e.

That is, the field generator 300 may be disposed inside the ultrasonic probe 20e, and the sensor unit 100e may be disposed outside the ultrasonic probe 20e.

In this case, the first position detection unit 210 including the field generator 300 may generate a magnetic field within a predetermined range from a region in which the second position detection unit 220 including the sensor unit 100e is located.

The second position detection unit 220 including the sensor unit 100e may detect the magnetic field formed by the first position detection unit 210 including the field generator 300, and may provide the position information detected in the three-dimensional space to the ultrasonic imaging apparatus 1.

While the present disclosure has been particularly described with reference to specific embodiments, but the scope of rights of the present disclosure is not limited to these embodiments.

Various embodiments that may be modified or modified by those skilled in the art of the present disclosure would also be within the scope of the present disclosure, without departing from the gist of the present disclosure specified in the claims.

The invention claimed is:

1. An ultrasonic probe comprising:
a case;
a transducer disposed inside the case;
a biopsy needle configured to be inserted into an object at a position adjacent to the case; and
a sensor unit comprising a sensor configured to measure the position of the biopsy needle and disposed inside the transducer,
wherein the transducer comprises a piezoelectric layer configured to generate ultrasonic waves, a sound absorbing layer disposed on one side of the piezoelectric layer to absorb the ultrasonic waves generated from the piezoelectric layer, and a sound absorbing member disposed on one side of the sound absorbing layer,
the sensor unit is disposed inside of the sound absorbing member,
the transducer further comprises a ground substrate disposed on one side of the piezoelectric layer, and a signal substrate disposed on the other side of the piezoelectric layer to be disposed at an inner side of the ground substrate, and
the sensor unit is disposed at an inner side of the signal substrate.

2. The ultrasonic probe according to claim 1, wherein the biopsy needle is magnetized, and
the sensor is configured to measure the position of the magnetized biopsy needle through a magnetic field generated by the magnetized biopsy needle.

3. The ultrasonic probe according to claim 2, wherein the transducer further comprises an acoustic layer having a non-magnetic material to prevent interference with the reception of the magnetic field of the sensor unit.

4. The ultrasonic probe according to claim 1, wherein the sensor unit further comprises a sensor substrate disposed at the inner side of the signal substrate to mount the sensor.

5. The ultrasonic probe according to claim 4, wherein the sensor substrate comprises a first sensor substrate provided on one side of the inside of the sound absorbing member, and a second sensor substrate provided on the other side of the inside of the sound absorbing member to be spaced apart from the first sensor substrate.

6. The ultrasonic probe according to claim 5, wherein the sensor comprises a first sensor mounted on the first sensor substrate and a second sensor mounted on the second sensor substrate, and
the first sensor and the second sensor face each other.

7. The ultrasonic probe according to claim 5, wherein the sensor comprises a first sensor mounted on the first sensor substrate and a second sensor mounted on the second sensor substrate, and
the first sensor and the second sensor are disposed adjacent to an inner surface of the sound absorbing member to face the signal substrate.

8. The ultrasonic probe according to claim 7, wherein the sensor unit further comprises a heat radiation sheet disposed on an inner surface of the sensor substrate.

9. The ultrasonic probe according to claim 8, wherein the sensor unit further comprises a stabilizer connected to the heat radiation sheet so that the heat radiation sheet radiates heat from the sensor and disposed at one end of the sound absorbing member.

10. The ultrasonic probe according to claim 5, wherein a distance by which the first sensor substrate and the second sensor substrate are spaced apart from each other is 10 to 60 times an acoustic wavelength of the transducer.

11. The ultrasonic probe according to claim 1, wherein the sensor is mounted on an inner surface of the signal substrate.

12. The ultrasonic probe according to claim 1, wherein the sensor is mounted on an inner surface of the ground substrate.

13. The ultrasonic probe according to claim 1, wherein the sensor unit is disposed inside a cover member provided to cover the outside of the transducer to prevent a disinfectant from penetrating into the sensor unit.

14. The ultrasonic probe according to claim 1, further comprising
a lens provided to transmit an ultrasonic signal generated from the transducer to the outside of the case,
wherein the lens and the case are combined by a molding process.

* * * * *